| United States Patent [19] | [11] | 4,339,533 |
|---|---|---|
| Chu | [45] | Jul. 13, 1982 |

[54] STABILIZATION OF CREATINE KINASE (CK) AND ITS APPLICATION AS A REFERENCE STANDARD

[75] Inventor: Douglas K. Chu, Yorktown Heights, N.Y.

[73] Assignee: Technicon Instruments Corporation, Tarrytown, N.Y.

[21] Appl. No.: 173,650

[22] Filed: Jul. 30, 1980

[51] Int. Cl.$^3$ .............................................. C12Q 1/50
[52] U.S. Cl. .................................... 435/17; 435/184; 435/188; 435/194
[58] Field of Search ...................... 435/4, 17, 184, 188, 435/194

[56] References Cited

U.S. PATENT DOCUMENTS

| 4,012,286 | 3/1977 | Sanderson et al. | 435/17 |
| 4,118,279 | 10/1978 | Determann et al. | 435/188 |
| 4,277,562 | 7/1981 | Modrovich | 435/15 |

OTHER PUBLICATIONS

Barbehenn et al., "Activation of Chicken Liver Dehydrofolate Reductase by Tetrathionate," *Biochem. Biophys. Res. Comm.*, Nov. 1978, pp. 402–407.
O'Sullivan, Int'l Journal of Protein Research, III, pp. 139–147 (1971).
Jacobs et al., Clinica Chimica Acta, 85, 299–309 (1978).
Smith et al., Biochemistry 14, 766–771 (1975).
Nealon et al., Clinical Chemistry 23, No. 5, 1977, pp. 816–829.
G. Szasz, Proceedings of the Second International Symposium on Clinical Enzymology, III, 1–9, 1975.

*Primary Examiner*—Peter A. Hruskoci
*Attorney, Agent, or Firm*—Morgan, Finnegan, Pine, Foley & Lee

[57] ABSTRACT

A stable intermediate composition of human or animal serum or a protein solution which contains a stable component consisting essentially of a mixed disulfide or dithiosulfonate derived from creatine kinase (ATP: creatine N-phosphotransferase, EC 2.7.3.2) is disclosed as well as its employment as a reference standard for the assay of creatine kinase.

27 Claims, No Drawings

STABILIZATION OF CREATINE KINASE (CK) AND ITS APPLICATION AS A REFERENCE STANDARD

BACKGROUND OF THE INVENTION

This invention relates generally to a stabilized form of enzyme creatine kinase (CK) which will be stable in serum and will adequately mimic CK in human samples for assay by various analytical procedures for determination of CK in human serum.

It is well known that the instability of many sulfhydryl (SH) containing enzymes are mainly due to the irreversible modification of the reactive SH group. CK is an example of such an enzyme that is present in human serum and is commonly measured for the purpose of diagnosing myocardial infarction. In the application of various assays for CK in human serum for this purpose, it is required to have available controls, calibrators and other reference materials which contain a known amount or concentration of this enzyme (CK). It is a general objective to achieve maximum stability of all the parameters in such reference materials, and it is known that CK is one of the less stable compounds added to such reference materials, by virtue of its reactive SH group. Therefore, the present invention aims to achieve a modified form of CK that will have increased stability in reference materials, specifically increased stability in the lyophilized material after reconstitution by addition of diluent. At the same time it is essential that the stabilized CK used in such products will adequately mimic the CK present in various human serum samples, for different analytical procedures used to determine CK.

In order to preserve the enzyme activity of CK and other SH-containing enzymes traditionally one or more thiol-compounds are added to the CK solution at high concentration. This approach cannot be used in the present instance, because such thiol compounds will interfere with other analytical procedures for the determination of other constituents of such reference materials. An example is the determination of alkaline phosphatase, which shows reduced enzymatic activity in the presence of excess added thiol—due to complexation of the zinc contained in the active site of this enzyme.

Another approach to stabilizing—SH enzymes is through modification of the reactive—SH groups by some reagent. However, generally such reagents, e.g. iodoacetate, lead to irreversible reaction of the SH group and considerable or total loss in enzyme activity. This is also undesirable for the preparation of stabilized CK to be used in a reference material.

It has been found that the reaction of an organodisulfide, preferably cystine, gives a stabilized CK which is uniquely useful in meeting all the requirements of a stabilized CK to be included in reference serum. It is highly stable upon reconstitution and it is converted to the active form very quickly in solutions used to assay for CK. Thus, it perfectly mimics CK in human serum and serves as an effective reference material.

SUMMARY OF THE INVENTION

In accordance with this invention, there is claimed a stable intermediate composition for incorporation into a diagnostic reference standard for the assay of creatine kinase (CK) in an aqueous solution which consists essentially of human or animal serum or a protein solution and a stable component consisting essentially of a mixed disulfide or dithiosulfonate derived from creatine kinase.

Preferably, the disulfide component is produced from an organodisulfide reactant, e.g., cystine, and the enzyme source is selected from beef heart, pig heart or rabbit muscle. The CK can also be obtained from human muscle. The reactant can be either natural cystine or cystine produced from cysteine under oxidizing conditions.

The above stable intermediate is employed with a thio-activating agent, preferably N-acetylcysteine or cysteine, to provide a stable reference standard for the assay of CK.

Human or animal serum, as used herein, means serum having a level of CK activity of less than about 10 U/l. If it is higher, said serum is treated to inactivate endogenous enzyme activity to provide a serum with a CK level of less than 10 U/l.

In one embodiment, the mixed disulfide derived from CK is obtained by reacting enzyme CK, derived from an animal source, with an excess of an organodisulfide at a temperature of from about 0° C. to about 40° C. under aqueous conditions.

The reaction product may be separated by various techniques, e.g. dialysis, ultrafiltration or gel filtration.

In another embodiment, the mixed disulfide derived from CK is obtained by reacting enzyme CK with an organothiosulfonate or an organothioacetate.

In another embodiment, the dithiosulfonate derived from CK is obtained by reacting enzyme CK with tetrathionate (sodium or potassium salt).

In still another embodiment, the mixed disulfide derived from enzyme CK is obtained in situ by the addition of excess organodisulfide to an enzyme (CK)-containing serum or protein solution, or by the addition of enzyme (CK) to an organodisulfide-containing serum or protein in solution.

DETAILED DESCRIPTION OF THE INVENTION

The present invention describes and claims a stable intermediate composition, its employment as a reference standard for the assay of CK, means for preparing a stabilized form of enzyme CK and its use in preparing other useful compositions.

The stable intermediate composition consists essentially of human or animal serum or a protein solution and a stable component consisting essentially of a mixed disulfide or dithiosulfonate derived from CK.

The enzyme source is suitably selected from beef heart, pig heart or rabbit muscle. These source materials are readily available and provide a stabilized form of CK which, for assay purposes, suitably mimics CK in human samples. The enzyme source need not be in a purified state. It can be crude to the extent of 50% or less.

The abovesaid stable component consisting essentially of a mixed disulfide or dithiosulfonate derived from CK is obtained in any one of the following ways:

(i) Reacting an organodisulfide with CK;
(ii) reacting an organothiosulfonate or an organothioacetate with CK;
(iii) reacting a tetrathionate with CK; or
(iv) forming the mixed disulfide or dithiosulfonate in situ by adding an excess of oganodisulfide (or organothiosulfonate or organothioacetate) or tetrathionate to a CK-containing serum or protein solution, or by adding CK to an organodisulfide (or organothiosulfonate or organothioacetate)-containing or tetrathionate-containing serum or protein solution.

In the first procedure, the organodisulfide used to prepare the reaction product is any disulfide which reacts with CK to provide a stabilized form of CK and which can be effectively activated during assay without interference from the other constituents of the reference materials.

Preferred organodisulfides include cystine, oxidized glutathione and dithiobisnitrobenzoic acid. Most preferred is cystine.

The reaction product can be formulated directly with the serum or first removed from the reaction mixture by dialysis prior to formulation.

The resulting intermediate composition will preferably contain reaction product in an amount of from 25 to about 2000 units/l./equivalent based on the total formulation, most preferred is a concentration of about 100–1000 units/l./equivalent.

In the second procedure (ii), the organothiosulfonate or organothioacetate selected depends on the mixed disulfide which one wants to obtain. The corresponding organothiosulfonate or organothioacetate is selected to provide the same mixed disulfide as obtained from cystine. The corresponding thiosulfonates or thioacetates are used to prepare mixed disulfides which are obtained from oxidized glutathione or dithiobisnitrobenzoic acid.

In the third procedure (iii), the reaction product, dithiosulfonate, is prepared from CK and tetrathionate.

The general synthetic procedure is carried out similarly to that outlined for (i) above.

In the fourth procedure, the mixed disulfide is formed in situ. This is accomplished in one of two ways. The first comprises adding an excess amount of organodisulfide, e.g. cystine, to a CK-containing serum. Upon addition, the cystine reacts with the enzyme CK with the formation, in situ, of the disulfide component consisting of the mixed disulfide derived from CK and cystine.

The similar procedure is followed to form the mixed disulfide in situ by substituting organothiosulfonate or organothioacetate for the organodisulfide.

To form dithiosulfonate in situ, tetrathionate is reacted with enzyme CK.

As an illustration of this method, one adds enzyme CK to a human serum so that the level of activity of enzyme in the resulting serum is about 500 I.U./l/equivalent.

To this CK-containing serum is added 10 mg/dl. of cystine. Upon mixing, the reaction product between enzyme CK and cystine results and the disulfide component forms in situ. The resulting composition is a stable intermediate composition for incorporation into a diagnostic reference standard for the assay of CK in an aqueous solution sample.

Alternatively, the same intermediate composition can be prepared by adding enzyme CK to a serum sample which contains an organodisulfide, e.g. cystine. To illustrate, to 100 ml. of serum containing 10 mg./dl. of cystine is added enzyme CK (50 units). Upon mixing, the disulfide component forms in situ and provides the same stable intermediate composition as prepared above.

In all of the four procedures, (i), (ii), (iii) or (iv), a stable intermediate composition is formed for incorporation into a diagnostic reference standard for the assay of creatine kinase in an aqueous solution sample. Of course, other reference materials, known in the art, are added to prepare the reference standard.

The above resulting intermediate composition can be stored, in lyophilized form, for substantial periods of time. When ready for assaying, the lyophilized material is reconstituted, and at the time of assayings, the thio-activating agent is often combined with the assay reagents.

The thio-activating agent can be selected from 1,3 dimercapto-2-propanol, 2,3 dimercapto-1-propanol, 1,2 dimercapto-ethane, glutathione (GSH), L-cysteine, L-cysteinemethyl ester, L-cysteineethyl ester, N-acetyl-L-cysteine (NAC), N-acetyl-DL-isocysteine, 2-aminoethylisothiouronium bromide (AET), dithiothreitol (DTT), dithioerythreitol (DTE), mercaptoethanol (ME), thioglycolic acid (TGA).

Preferred thio-activating agents are cysteine and N-acetyl-cysteine.

The reaction product, stabilized CK, disclosed herein is obtained in one manner by reacting CK, derived from an animal source, with an excess of an organodisulfide at a temperature of from about 0° C. to about 40° C. under aqueous conditions.

The resulting reaction product can be separated from the reaction mixture to remove any excess organodisulfide and other low molecular weight compounds by dialysis, ultrafiltration or gel filtration.

The reaction product, as obtained above, can be formulated with human or animal serum and stored. When used for assaying purposes, the resulting serum formulation is combined with a thio-activating agent, as described above, together with materials commonly used for reference purposes.

EXAMPLE I

A. Preparation of Stabilized Enzyme

An aqueous solution of CK enzyme, derived from pig heart (6600 I.U.) is combined with 2.1 mg. of cystine. The reaction mixture (2 ml.) is stirred at 25° C. for 60 minutes.

To above procedure is repeated except instead of pig heart, the enzyme CK is derived from rabbit muscle and beef heart.

B. Preparation of Serum Formulation

To 30 μl. of each of the above reaction mixture is added 200 ml. of deactivated bovine serum (initial CK concentration less than 10 U/l. The resulting formulations contain about 500 units/l./equivalent of CK enzyme.

The stability of the resulting serum formulation is demonstrated hereinbelow:

| Source | Treatment | % CK Activity Room Temp., 24 Hours |
| --- | --- | --- |
| Beef Heart | None | 82.3 |
|  | Cystine | 101.5 |
| Pig Heart | None | 85.1 |
|  | Cystine | 99.0 |
| Rabbit Muscle | None | 83.0 |
|  | Cystine | 100.2 |

In each formulation, the inclusion of cystine in the formulation results in a stable formulation without loss of activity even after 24 hours. Without cystine, the formulation severely diminished in activity after 24 hours.

ASSAY

To each of the serum formulations above (50 μl.) is added 2.5 ml. of an assay solution.*

*"Single Vial" CK-NAC, activated, a trademarked product of Bio-Dynamics/BMC containing the thio-activator N-acetyl-L-cysteine.

The chemistry involved in the assay can be shown as follows:

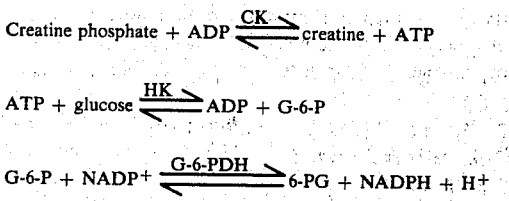

Creatine phosphate + ADP $\xrightleftharpoons{CK}$ creatine + ATP

ATP + glucose $\xrightleftharpoons{HK}$ ADP + G-6-P

G-6-P + NADP$^+$ $\xrightleftharpoons{G\text{-}6\text{-}PDH}$ 6-PG + NADPH + H$^+$ in which the following designations are used:
ADP=adenosine-5'-diphosphate
ATP=adenosine-5'-triphosphate
HK=hexokinase (ATP: D-hexose-6-phosphotransferase EC 2.7.1.1)
G—6—P=glucose-6-phosphate
NADP$^+$=nicotinamide-adenine-dinucleotide phosphate
6-PG=6-phosphogluconate
NADPH=nicotinamide-adenine-dinucleotide phosphate, reduced The formation of NADPH proceeds at the same rate as the formation of creatine in equimolar amounts. The rate at which the NADPH is formed may be determined photometrically at 340 nm by the increase in absorbance, and is directly proportional to the enzyme activity.

Such assays are typically carried out on suspected myocardial infarct blood samples. A sharp increase in CK levels is indicative of a myocardial infarction.

EXAMPLE II

The procedure of Example I is repeated except that instead of cystine the following reagents are used:
oxidized glutathione
dithiobisnitrobenzoic acid

EXAMPLE III

The procedure of Example I is repeated except that instead of cystine, the following organothiosulfonate and organothioacetate are used to formulate similar stabilized enzyme and serum formulations:
1-Amino-1-Carboxy-Ethyl Methanethiosulfonate
1-Amino-1-Carboxy-Ethyl Thioacetate

EXAMPLE IV

The procedure of Example I is repeated except that instead of cystine, sodium tetrathionate is used to formulate similar stabilized enzyme and serum formulations.

EXAMPLE V

The serum formulations described in Example I are lyophilized as follows:
bottles containing 10 ml. each of the formulated serum are first frozen in a lyophilizer at −45° C. The water in the frozen serum is sublimated under vacuum at shelf temperature of about 25° C. The bottles containing the moisture-free lyophilized cakes are then sealed under nitrogen atmosphere;

and reconstituted as follows:
10 ml. of cold (4° C.) distilled water or buffer solution is added to the lyophilized serum cake and mixed.

EXAMPLE VI

The assay procedure of Example I wherein the following thio-activators are included instead of N-acetyl-cysteine:
1,3 Dimercapto-2-propanol
2,3 Dimercapto-1-propanol
1,2 Dimercapto-ethane
Glutathione (GSH)
L-Cysteine
L-Cysteinemethyl ester
L-Cysteineethyl ester
N-Acetyl-L-cysteine (NAC)
N-Acetyl-DL-isocysteine
2-Aminoethylisothiouronium bromide (AET)
Dithiothreitol (DTT)
Dithioerythreitol (DTE)
Mercaptoethanol (ME)
Thioglycolic acid (TGA)
with comparable results.

EXAMPLE VII

The procedure of Example I for preparing stabilized enzyme is repeated in which the reaction product is further treated by the following:
(a) Dialysis
(b) Ultrafiltration
(c) Gel filtration

EXAMPLE VIII

The procedure of Example I is repeated for making serum formulations in which human serum or a protein solution (e.g. bovine serum albumin, 6 g./dl.) are used instead of bovine serum with comparable results.

EXAMPLE IX

The following procedures are employed to prepare a stable intermediate composition for incorporation into a diagnostic reference standard for the assay of CK in an aqueous solution sample.
(a) To a human serum pool (100 ml.) is added CK (50 units). The resulting sample has a level of CK activity of about 500 units/l./equivalent. To this is added cystine (10 mg.). The resulting intermediate has a level of CK activity of about 500 units/l./equivalent.
(b) To a human serum pool (100 ml.) is added cystine (10 mg.). To this is added CK (50 units) and the resulting intermediate composition has a level of CK activity of about 500 units/l./equivalent.

It should be understood by those skilled in the art that various modifications may be made in the present invention without departing from the spirit and scope thereof as described in the specification and defined in the appended claims.

What is claimed is:
1. A stable intermediate composition for incorporation into a diagnostic reference standard for the assay of creatine kinase (CK) in an aqueous solution sample which consists essentially of human or animal serum or a protein solution selected from bovine or human serum albumin and an effective amount of a stable component consisting essentially of a mixed disulfide or dithiosulfonate derived from creatine kinase.

2. The intermediate compositon of claim 1 wherein said mixed disulfide is derived from creatine kinase and an organodisulfide selected from cystine, oxidized glutathione and dithiobisnitrobenzoic acid.

3. The intermediate composition of claim 2 wherein said organodisulfide is cystine.

4. The intermediate composition of claim 2 wherein said mixed disulfide is present in an amount of from about 25 to about 2000 units/l./equivalent of the total formulation.

5. The intermediate composition of claim 1 wherein said mixed disulfide is derived from creatine kinase and an organothiosulfonate or an organothioacetate.

6. The intermediate composition of claim 1 wherein said dithiosulfonate is derived from creatine kinase and a tetrathionate.

7. The intermediate composition of claim 1 wherein said mixed disulfide is derived in situ by the addition of excess organodisulfide or organothiosulfonate or organothioacetate to a CK-containing serum or protein solution, or by the addition of CK to an organodisulfide or organothiosulfonate or organothioacetate-containing serum or protein solution.

8. The intermediate composition of claim 1 wherein said dithiosulfonate is derived in situ by the addition of excess tetrathionate to a CK-containing serum or protein solution, or by the addition of CK to tetrathionate-containing serum or protein solution.

9. The intermediate composition of claim 1 wherein said creatine kinase enzyme source is selected from beef heart, pig heart or rabbit muscle.

10. The intermediate composition of claim 1 in lyophilized form.

11. The intermediate composition of claim 1 in reconstituted form.

12. A stable reference standard for the assay of creatine kinase (CK) which comprises the stable intermediate composition of claim 1 and a thio-activating agent.

13. The reference standard of claim 12 wherein said thio-activating agent is selected from 1,3 dimercapto-2-propanol, 2,3 dimercapto-1-propanol, 1,2 dimercapto-ethane, glutathione (GSH), L-cysteine, L-cysteinemethyl ester, L-cysteineethyl ester, N-acetyl-L-cysteine (NAC), N-acetyl-DL-isocysteine, 2-aminoethylisothiouronium bromide (AET), dithiothreitol (DTT), dithioerythreitol (DTE), mercaptoethanol (ME), thioglycolic acid (TGA).

14. The reference standard of claim 13 wherein said thio-activating agent is cysteine.

15. The reference standard of claim 13 wherein said thio-activating agent is N-acetylcysteine.

16. A method of preparing a stable intermediate composition for incorporation into a diagnostic reference standard for the assay of creatine kinase (CK) which comprises reacting enzyme creatine kinase (CK), derived from an animal source, with an excess of an organodisulfide at a temperature of from about 0° C. to about 40° C. under aqueous conditions to form a reaction product consisting essentially of a mixed disulfide derived from said creatine kinase, and combining an effective amount of said mixed disulfide with human or animal serum, or a protein solution selected from bovine or human serum albumin to form said stable intermediate composition.

17. The method of claim 16 wherein said organodisulfide is selected from cystine, oxidized glutathione and dithiobisnitrobenzoic acid.

18. The method of claim 17 wherein said organodisulfide is cystine.

19. The method of claim 16 further comprising the step of dialyzing the reaction mixture to remove excess organodisulfide and other low molecular weight compounds.

20. The method of claim 19 subsequent to dialysis, the reaction product is lyophilized.

21. The method of claim 16 further comprising a separation step to recover reaction product selected from ultrafiltration and gel filtration.

22. The method of claim 16 wherein said creatine kinase enzyme source is selected from beef heart, pig heart or rabbit muscle.

23. The method of claim 16 wherein human or animal serum is combined to provide said stable intermediate composition.

24. A method of preparing an intermediate composition reference standard for the assay of creatine kinase (CK) which comprises adding a thio-activating agent to the composition obtained by the method of claim 23.

25. The method of claim 24 wherein said thio-activating agent is selected from 1,3 dimercapto-2-propanol, 2,3 dimercapto-1-propanol, 1,2 dimercapto-ethane, glutathione (GSH), L-cysteine, L-cysteinemethyl ester, L-cysteineethyl ester, N-acetyl-L-cysteine (NAC), N-acetyl-DL-isocysteine, 2-aminoethylisothiouronium bromide (AET), dithiothreitol (DTT), dithioerythreitol (DTE), mercaptoethanol (ME), thioglycolic acid (TGA).

26. The method of claim 25 wherein said thio-activating agent is cysteine.

27. The method of claim 25 wherein said thio-activating agent is N-acetyl cysteine.

* * * * *